United States Patent [19]

Tayot et al.

[11] Patent Number: 5,201,745
[45] Date of Patent: Apr. 13, 1993

[54] VISCERAL SURGERY PATCH

[75] Inventors: Jean-Louis Tayot, La Tour De Salvagny; Jacques Marescaux, Scharrachbergheim; Henri Dumas; Michel Tardy, both of Lyon, all of France

[73] Assignee: Imedex, Lyon, France

[21] Appl. No.: 746,199

[22] Filed: Aug. 15, 1991

Related U.S. Application Data

[63] Continuation of Ser. No. 458,748, filed as PCT/FR89/00108 Mar. 15, 1989, published as WO89/08467 Sep. 21, 1989, abandoned.

[30] Foreign Application Priority Data

Mar. 15, 1988 [FR] France ................. 8803321

[51] Int. Cl.⁵ ............... A61B 17/00; A61F 13/00; A61L 13/00
[52] U.S. Cl. ...................... 606/151; 602/50; 424/428; 424/444; 600/37; 623/11; 623/66
[58] Field of Search ............... 128/156; 424/426, 444; 600/37; 606/151; 623/11, 15, 66; 602/50

[56] References Cited

U.S. PATENT DOCUMENTS

| | | | |
|---|---|---|---|
| 3,272,204 | 9/1966 | Artandi et al. | 606/151 |
| 3,491,760 | 1/1970 | Braun et al. | 623/1.5 |
| 3,526,228 | 9/1970 | Lyng | 606/151 |
| 4,291,013 | 9/1981 | Wahlig et al. | 623/11 |
| 4,403,604 | 9/1983 | Wilkinson et al. | 600/37 |

FOREIGN PATENT DOCUMENTS 0227955  7/1987  European Pat. Off.

Primary Examiner—Randall L. Green
Assistant Examiner—Paul Prebilic
Attorney, Agent, or Firm—Larson and Taylor

[57] ABSTRACT

A patch for visceral surgery is made from a biomaterial consisting of two layers of collagen superimposed and closely combined, namely a porous adhesive layer of fibrous collagen and a film of collagen and/or gelatin.

14 Claims, No Drawings

VISCERAL SURGERY PATCH

BACKGROUND OF THE INVENTION

This application is a continuation of application Ser. No. 07/458,748 filed as PCT/FR89/00108 filed Mar. 15, 1989, published as WO89/08467 Sep. 21, 1989, now abandoned.

This invention relates to the use of a collagen-based biomaterial to make a visceral surgery patch.

In visceral surgery one often meets with post-surgical accidents due to a defective healing of viscera. Now the fact is that the lack of healing of the viscera is the main source of mortality, morbidity and excess costs in visceral and particularly in digestive surgery.

Nevertheless no satisfactory solution has yet been found to this healing problem, which is aggravated when the context is unfavorable, for instance in the case of a digestive fistula, a septic environment or again in the case of a chemical aggression, notably a biliary one, &c.

Whereas differing specialized surgical fields widely benefit from more and more advanced biomaterials, visceral surgery, particularly digestive surgery, has neglected this track.

SUMMARY OF THE INVENTION

Aim of this invention is to solve this problem by providing a visceral surgery patch made from a biomaterial and allowing a satisfactory healing of the viscera, even under unfavorable conditions.

Another aim of the invention is to provide a visceral surgery patch which is made from an easily adhering biomaterial.

Still another aim of the invention is to provide a visceral surgery patch which is made from a wholly biodegradable biomaterial, and which yields an excellent confinement and hemostasis effect by temporarily replacing the wall to be restored.

Still another aim of the invention is to offer a visceral surgery patch made from a biomaterial based on compounds which are naturally found in tissues and which undergo a minimum of alterations.

Still another aim of the invention is to provide a visceral surgery patch made from a biomaterial which is mechanically resistant as well in dry form as after rehydration in a physiological fluid, and which is deprived of any chemical toxicity.

Still another aim of the invention is to provide a visceral surgery patch made from a biomaterial made up of collagen only, plus possibly gelatin, and which may be easily colonized by cells from the organism.

Another aim of the invention is to provide a visceral surgery patch made from a biomaterial which is perfectly tolerated by the patient.

Still another aim of the invention is to provide a visceral surgery patch made from a biomaterial based on human collagen which may be obtained in sufficient amount.

By visceral surgery is meant notably digestive surgery, that is to say oesophageal, gastric, duodenal, intestinal, rectal, pancreatic and hepato-biliary surgery, as well as surgery of the trachea, the urogenital tract and neurosurgery.

Aim of the invention is a visceral surgery patch, characterized in that it is made from a biomaterial formed from two superimposed and intimately associated collagen layers, that is to say a porous layer, preferably a stickable one, of fibrous collagen, and a collagen and/or gelatin film.

A particular efficiency is obtained if the patch, while retaining sufficient mechanical qualities, has a total density which is not above about 8 $mg/cm^2$, and patches satisfying this prerequisite are preferred.

One prefers particularly a patch whose porous layer has a density of about 2 $mg/cm^2$ and whose film has a density of about 1 $mg/cm^2$.

Fibrous appearance means the macroscopic appearance of collagen in dry state after freeze-drying or treatment with aceton even if for some kinds of collagen like type IV collagen no microscopic fibers may be observed after solubilization.

In an embodiment of the invention the patch is obtained by casting the collagen solution which is to form the collagen film onto a fibrous layer whose shapes and dimensions correspond to those of the patch, and into which it is at least partially impregrated.

In another embodiment of the invention, the patch is obtained by cutting out, following the dimensions and shapes of the patch, a biomaterial sheet made up by casting a collagen solution intended to form the collagen film, onto a fibrous collagen layer into which it is at least partially impregnated.

The collagen which is used in the invention may be in a non-cured form, or cured by gentle curing, notably by a treatment with periodic acid, such as the gentle curing process with periodic oxidation as described in French Patent Application No 2 601 371. This process does not entail any toxic hazard.

The invention also provides for the use of a mixture of cured and non-cured collagens.

The selection of the collagen quality will depend upon the desired biodegradability level.

The collagen which is used is preferably human type I, III ou IV collagen, or a mixture of these (French Patent Application Nos 2 597 499 and 2 586 703 to Institut Mérieux) as well for the fibrous layer as for the overlying film.

This collagen may or not be oxided according to the process described in French Patent Application No 2 601 371 and be used as such or as a mixture with the non-oxided collagen.

The oxided collagen fraction in relation to the non-oxided collagen may be 0–100%, it being understood that a preferred fraction interval is the following: 20% oxided collagen and 80% native collagen.

In another embodiment the film is made from soluble collagen which is enriched in type III+I.

In another particular embodiment the collagen is replaced by gelatin (a substance derived from collagen) in the film.

Preferably the film reproduces in the most precise manner the natural conditions for the transmission of moisture and other exchange phenomena. More precisely the film is permeable to ions and metabolites, including dissolved gases, and impervious to proteins and bacteria.

In all cases wherein the biomaterial is to be in direct contact with the patient, the collagen, be it intended for the fibrous layer or the film, will preferably be of human, and notably placental, origin.

The film thickness is preferably between 5–250 microns, notably between 10–50 microns, for example about 20 microns in the dry state. In the wet state, the thickness is preferably between 10–500 microns, and notably between 20–100 microns, for instance about 40 microns.

The thickness of the fibrous layer is preferably between 100 microns–8 mm and, notably, about 1 mm in the dry state, and about the same in the wet state.

Preferably, the film contains in the wet state 15–70% collagen and in the dry state 40–100% collagen.

Preferably, the fibrous layer contains, in the wet or in the dry state, 2–30% collagen, preferably 5–20%.

DETAILED DESCRIPTION OF THE INVENTION

This invention will now be described in detail with the help of non-limiting examples showing several embodiments. Naturally one can make either a sheet of biomaterial which will then be cut out according to the desired patch dimensions and shape, or directly a biomaterial having the shapes and dimensions of the patch. The following examples relate to the latter possibility, with the desired patch being selected as rectangular and having dimensions of about 5×7×0.08 cm.

Preparation of the Fibrous Layer

Starting from an acid type I, III, or I+III collagen solution one makes a precipitation, preferably with the help of sodium phosphate. The precipitate is then frozen and freeze-dried. The obtained compress is then packed down so as to make the fibrous layer which then has the appearance of a thin dehydrated sheet of neutral pH, porous and very dense.

As a variant, starting from a neutral type IV collagen solution which may contain a curing agent such as collagen oxided with periodic acid and possibly glycerin, one freezes and freeze-dries, then packs down the obtained compress so as to obtain the fibrous layer.

EXAMPLE 1

1 volume $Na_2HPO_4$ (0.2M, pH 7.5) is mixed with 9 volumes of an acid III+I collagen solution (collagen III+I prepared according to the process described in French Patent Application No 2 597 499) at a concentration of 0.125% in distilled water at 20° C. A precipitation follows. The precipitation lasts between 4–15 hours and the precipitate is collected by centrifugation.

The precipitate is then adjusted to a concentration of 0.5–3% collagen and 0.5–3% glycerin before being frozen and freeze-dried.

The obtained compress (dimensions 5×7×0.8 cm) is packed down to yield a fibrous, scarcely hydrophilic sheet (dimensions 5×7×0.08 cm).

EXAMPLE 2

Into an acid III+I collagen solution (collagen III+I prepared according to the process described in French Patent Application No 2 597 499) at a concentration of 0.125% in distilled water at 20° C., is added, with shaking, a periodic acid solution so as to obtain a final concentration of 0.002M.

After shaking for 2 hours at room temperature $Na_2HPO_4$ (0.2M, pH 7.5) is added in an amount of 9 volumes of III+I collagen for 1 volume of $Na_2HPO_4$. A precipitation follows.

The precipitation lasts between 4–15 hours and the precipitate is collected on Nylon cloth or by centrifugation.

A further step for washing the precipitate may be added after this step.

One then resumes the post-precipitation steps of Example 1.

EXAMPLE 3

This relates to bovine type I collagen. One resumes Example 1.

EXAMPLE 4

This relates to bovine type I collagen as cured by periodic oxidation. One resumes Example 2.

EXAMPLE 5

One starts from a neutral aqueous solution containing 2% glycerin and 2% non-oxided human type IV collagen. One freezes and freeze-dries, then packs down the obtained compress.

EXAMPLE 6

One starts from an aqueous solution containing 2% glycerin and 2% collagen, that is to say 8 volumes non-oxided human type IV collagen for 2 volumes oxided human type IV collagen. One freezes and freeze-dries, then packs down the obtained compress.

EXAMPLE 7

One starts from an aqueous collagen solution obtained from a 1% oxided human type IV collagen solution to which human type I+III collagen has been mixed, in the form of fibrils or particles, at a concentration of 10–30 mg/ml. One freezes and freeze-dries, then packs down the obtained compress.

Preparation of the Material

Onto a very dense collagen sheet, cured or non-cured, described above, are cast:

EXAMPLE 8

2–10 ml of a mixture of an aqueous human collagen IV solution at a concentration which may reach 5% weight/volume, and another oxided human collagen IV solution (oxided collagen according to the process described in French Patent Application No 2 601 371) in the respective proportions of 0 to 100% after dehydration under a sterile laminar flow hood, a biomaterial made up of collagen only is obtained; this biomaterial is then sterilized; these dehydration and sterilization steps will not be repeated in the following examples; they will be understood.

In the following Examples, the smallest concentrations (0.2–1%) are preferred for cold collagen solutions and the highest concentrations (1–5%) may be used for tepid gelatin solutions.

EXAMPLE 9

2–10 ml of a non-oxided human collagen IV solution at a concentration of 0.2–5%;

EXAMPLE 10

2–10 ml of an oxided human collagen at a concentration of 0.2–5%;

EXAMPLE 11

2–10 ml of a solution containing 60–95% (Volume/Volume) human III+I collagen at a concentration of 1% and 40–5% (Volume/Volume) oxided human collagen IV;

EXAMPLE 12

2-10 ml of a human III+I collagen solution at a concentration of 0.2-5%;

EXAMPLE 13

10 ml of an oxided human III+I collagen solution (collagen oxided according to the process described in French Patent Application No 2 601 371) at a concentration of 0.2-5%;

EXAMPLE 14

10 ml of a bovine type I collagen solution, as blended, or not, in the proportions of Example 8 with oxided human collagen IV or oxided bovine collagen I;

EXAMPLE 15

10 ml of an oxided type I bovine collagen solution.

This process including casting a collagen or gelatin solution onto a dehydrated fibrous structure allows one to obtain some impregnation of said solution in the fibrous structure, which yields, after dehydration of the whole, to a mechanically very resistant inter-layer linkage.

The obtained dehydrated and sterilized biomaterial may whenever needed be rehydrated in a physiological fluid. This rehydration does not entail the loss of its mechanical resistance nor of its inter-layer cohesion. The obtained biomaterial is very flexible and can completely adapt to any contour.

Various uses of the collagen patch in visceral surgery will now be described in detail.

I. Use of the Collagen Patch for the Prevention and Treatment of Post-Operative Digestive Fistulae Anastomotic separations as a consequence of a lack of healing between two viscerae represent the main source of mortality, morbidity and excess costs in digestive surgery. In other words a process that could prevent the appearance of a post-operative anastomotic separation would represent a notable advance.

a). A Study of the Healing of an Intestinal Loss of Substance in a Favorable Context for the Healing Process After the occurrence of a 1 cm diameter loss of substance in the front face of the caecum of 56 male Wistar rats each loss of substance is sealed off with the help of a collagen IV patch of human origin, obtained by cutting out a biomaterial sheet so as to form 1.5 cm diameter disks, the collagen patch being linked to the rims of the loss of substance with a biological glue which is applied onto the fibrouss layer.

The animals were killed in series of 8 at days 5, 10, 15, 20, 30, 40 and 60 post-operation and have been studied macroscopically for adhesions and a possible retraction, and have also been studied with an optical microscope and a scanning microscope.

Mortality and morbidity attributable to the surgical technique were zero. On day 5 after operation the collagen patch is well fastened onto the caecum and seals off the breach perfectly. From day 5 to day 20 the intestinal loss of substance heals by degrees whereas the patch is partially resorbed or eliminated in the caecum lumen. On day 20 after operation the mucous membrane seems to be restored. Healing of the muscles begins on day 30 and on day 40 healing is completed.

This first experimental step allows one to assert that the collagen patch allows the healing of a healthy non-suturated loss of digestive substance.

Because healing problems generally appear under unfavorable general and local conditions the next step was to study the healing potential of the collagen patch after creation of a digestive fistula causing a severe denutrition and a local inflammatory response hardly susceptible to primary healing.

b). A Study of the Healing of a Colonic Fistula

A open colonic fistula is created on 106 Wistar rats. Each colonic fistula is closed in the third week with a patch of collagen IV of human origin, in the shape of a 1.5 cm diameter disk obtained as above. As a glue one uses a biological glue.

Samples are taken sequentially on days 5, 10, 15, 20, 30, 40 and 60 after operation.

Some animals die within 48 hours after the second operation because of the important denutrition generated by the fistula. None of the deaths could be attributed to a lysis of the patch. Healing is the same as that observed in case of a loss of healthy substance, but it is delayed. Reepithelialization is completed on day 30 only, and muscular healing is obtained on day 60 only.

c). A Study of the Healing of an Intestinal Anastomosis as Protected by a Patch in a Septic Local-Regional Context Anastomosis in a septic environment is considered as a hazardous suture, and is therefore condemned by a majority of authors whose recommendation is to refrain from making a suture in a first step.

112 rats are distributed into two groups, with control group 1 benefiting from a suture 12 hours after a peritonitis is created, and group 2 benefiting from a suture which is protected by a collagen patch according to the invention.

Results show a perfect digestive healing in group 2.

II. Use of the Collagen Patch in Biliary Surgery

Biliary leakage and stenosis are the main complications to be feared after opening of the main biliary tract.

To avoid the hazard of a premature biliary leakage which can lead to a biliary peritonitis one proceeds to make an external drain after every opening of the main biliary duct requiring a secondary suture. This technique is a demanding and prolonged one because it requires a 14-day treatment in hospital, the drain being removed on day 12 only, while causing pain to the patient.

A patch resisting biliary aggression would avoid this complication.

a). An In Vitro Study: the Physical Resistance of the Collagen Patch to Biliary Aggression Collagen patch samples are incubated in human bile at 37° C. during 20 days.

The study of physical resistance is appreciated by a surface study with a scanning electron microscope, and with mechanical tests relating to the breakage strength and the distorsion of the sample when placed in an extensometer.

The surface study did not show any structural change on days 5, 7 and 20 after incubation.

Mechanical tests did not show any alteration after incubation in bile.

b). Use of the Collagen Patch in the Healing of a Non Suturated Bile Duct Injury in the Dog 10 dogs are subjected to a 1 cm longitudinal incision of the bile duct, 2 cm away from the upper limit of the first duodenum. This opening is not suturated but simply sealed off by sticking a collagen patch directly made wit the appropriate shape and dimensions.

The dogs are killed on day 30 after operation after intravenous cholangiography. A sample is taken from the zone which has been stuck and each sample taken is studied macroscopically, with an optical microscope and with a scanning electron microscope.

One can thus show that this biomaterial allows one to guarantee bilistasis, avoiding any post-operative bile leakage, and leads to bile duct healing without parietal ischemia.

III. Use of the Collagen Patch in Hepatic Surgery

The technique of hepatectomy is not without complications such as haemorrhages, bile leakages and subphrenic abscesses.

The test protocol relates to male Wistar rats. Each rat is subjected to an hepatic section on a lobe and a selective ligature of the left hepatic duct.

In the first, or control, group the slice of the left hepatic section is protected with biological glue, without any other measure being taken so as to cause hemostasis or bilistasis.

In a second group the slice of the hepatic section is protected with a collagen patch, stuck with biological glue.

Each series includes 40 animals which are sequentially killed on days 5, 10, 20 and 30 after operation, at a rate of 10 animals per period. Each piece of hepatectomy is studied macroscopically, with an optical microscope and with a scanning electron microscope, so as to study the integration of the patch as well as the progress of healing. Contrary to what can be observed in the first group the second group has no bile or blood leakage. The healing of bile ducts which were cut at the section slice is perfect.

The collagen patch therefore prevents biliary fistula after hepatectomy.

We claim:

1. A visceral surgery patch which is fully biodegradable comprising:
    a first biodegradable layer forming a film selected from the group consisting of biodegradable collagen, gelatin and mixtures thereof, and
    a second biodegradable porous layer of fibrous biodegradable collagen,
    said first and second biodegradable layers being directly superimposed and said first biodegradable layer at least partially impregnating said second biodegradable layer, and said patch having a density of at most 8 mg/cm$^2$.

2. A patch according to claim 1 made by the process of casting a collagen solution onto the second biodegradable layer whose shape and dimensions correspond to said patch, to form said first biodegradable layer superimposed over and at least partially impregnating said second biodegradable layer.

3. A patch according to claim 1, characterized in that the porous layer and film have respective densities of 2 and 1 mg/cm$^2$.

4. A patch according to claim 1, characterized in that the collagen of said first and second layers is non-cured collagen and/or collagen which has been subjected to gentle curing.

5. A patch according to claim 4, characterized in that the collagen is made of 80% of non-cured collagen and 20% of gently-cured collagen.

6. A pitch according to claim 4, characterized in that the gently cured collagen is cured by periodic oxidation.

7. A patch according to claim 4, characterized in that the second layer is made up of human type III+I fibrous collagen.

8. A patch according to claim 4, characterized in that the second layer is made up of human type IV fibrous collagen.

9. A patch according to claim 4, characterized in that the second layer is made up of a mixture of human type III, I and IV fibrous collagen.

10. A patch according to claim 4, characterized in that the collagen is made up of human type IV and/or type III+I collagen.

11. A patch according to claim 1, characterized in that the film is made up of gelatin.

12. A patch according to claim 1 characterized in that the second layer includes 2-30% collagen and the film includes 40-100% collagen.

13. A patch according to claim 1 characterized in that the thickness of the fibrous layer is between 100 microns and 8 mm.

14. A patch according to claim 1, characterized in that the film thickness is between 5-250 microns.

* * * * *